United States Patent [19]

Tontarra

[11] Patent Number: 5,607,449
[45] Date of Patent: Mar. 4, 1997

[54] TUBULAR-SHAFT SURGICAL INSTRUMENT

[75] Inventor: Thomas Tontarra, Wurmlingen, Germany

[73] Assignee: Tontarra Medizintechnik GmbH, Wurmlingen, Germany

[21] Appl. No.: 455,540

[22] Filed: May 31, 1995

[30] Foreign Application Priority Data

Nov. 15, 1994 [DE] Germany .............. 9418094 U

[51] Int. Cl.$^6$ .................................. A61B 17/28
[52] U.S. Cl. .............. 606/205; 606/208; 128/753
[58] Field of Search .................... 606/205, 206, 606/207, 51, 174, 128, 209; 128/751, 754, 755

[56] References Cited

U.S. PATENT DOCUMENTS

| 5,370,659 | 12/1994 | Sakashita | 606/205 |
| 5,483,952 | 1/1996 | Aranyi | 606/205 |
| 5,507,297 | 4/1996 | Slater et al. | 606/205 |

FOREIGN PATENT DOCUMENTS

| 3711377A1 | 10/1988 | Germany . |
| 9114306 | 3/1992 | Germany . |
| 9202132 | 6/1992 | Germany . |
| 9307793 | 9/1993 | Germany . |
| 9317535 | 3/1994 | Germany . |
| 4323093A1 | 1/1995 | Germany . |

*Primary Examiner*—Michael Powell Buiz
*Assistant Examiner*—Kevin Truong

[57] ABSTRACT

The tubular-shaft surgical instrument is provided with an actuating rod for the manual operation of a forceps-like or scissors-like tool, which actuating rod is guided axially movably in a guide tube. The tool is mounted at the free end of the guide tube, and it has at least one tool part pivotable around a pivot axis extending at right angles to the axis of the tube. The tool is detachably mounted in the front end of the guide tube in the manner of a bayonet catch. The actuating rod is connected at its rear end, by a detachable connection, to an actuating lever, which in turn is pivotably mounted on a holder provided with a handgrip. A guide sleeve, which is coaxial with the guide tube, and in which the actuating rod is prevented from rotating in relation to the guide tube by manually detachable rotation-preventing elements, is arranged in the holder. To make it possible to easily detach the actuating rod with the tool from the guide tube and from the holder, the actuating rod is designed such that it passes through the guide sleeve in one piece. Moreover, it is detachably connected to the actuating lever by a rod coupling, while the guide tube is rigidly and especially nonrotatably connected to the guide sleeve.

10 Claims, 3 Drawing Sheets

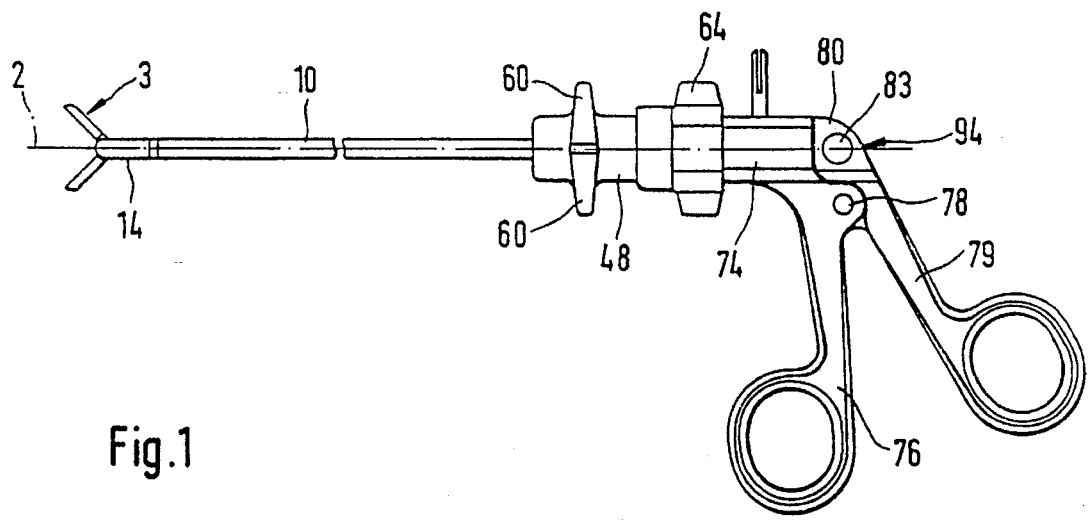
Fig.1
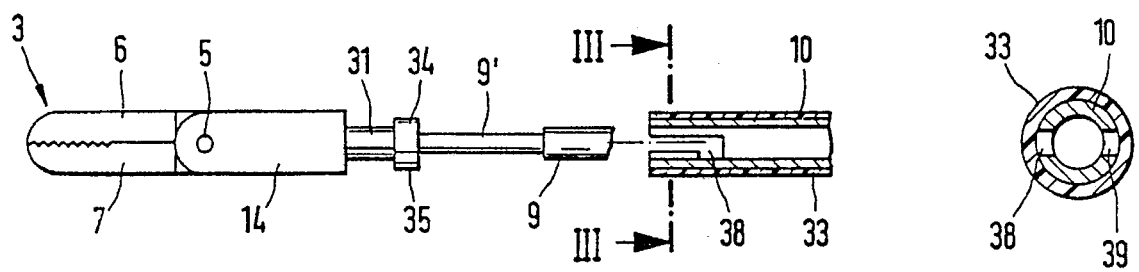
Fig.2
Fig.3
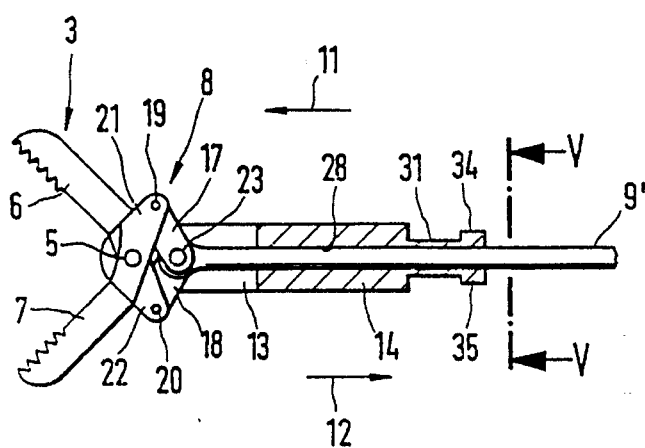
Fig.4
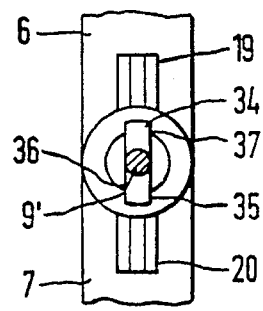
Fig.5

5,607,449

TUBULAR-SHAFT SURGICAL INSTRUMENT

FIELD OF THE INVENTION

The present invention pertains to a tubular-shaft surgical instrument with an actuating rod guided axially movably in a guide tube for a forceps-like or scissors-like tool, which is mounted at the free end of the guide tube in a tube section cut out in the form of a slot or a fork, has at least one tool part pivotable around a pivot axis extending at right angles to the axis of the tube, and which is detachably mounted in the front end of the guide tube in the manner of a bayonet catch, wherein the actuating rod is connected at its rear end by a detachable connection to an actuating lever, which in turn is pivotably mounted on a holder provided with a handgrip, and wherein the holder has a guide sleeve coaxial with the guide-tube, in which guide sleeve the actuating rod is secured against rotation in relation to the guide tube by manually detachable rotation-prevention elements.

BACKGROUND OF THE INVENTION

A tubular-shaft medical instrument of the type described in the introduction has been known (German Utility Patent No. DE-GM 93,17,535.3), which can easily be disassembled without the use of a tool and can therefore be cleaned and sterilized more easily and above all more thoroughly. At its holder-side end, the guide tube has a coupling sleeve, which is detachably connected to a coupling tube arranged in the guide sleeve in the manner of a bayonet catch. The actuating rod is detachably connected by a rod coupling to a coupling rod establishing the connection with the actuating lever. The actuating rod thus consists of two parts, which are or can be connected to one another by a manually detachable coupling.

In this prior-art tubular-shaft instrument, the removable guide tube with the actuating rod and the surgical tool can be rotated into any desired rotary position around the axis of the guide tube in relation to the holder by means of a rotary mount in the guide sleeve of the holder, and it can be fixed in a gradual locking manner by means of a rotation position-locking means.

However, the manufacture of such tubular-shaft instruments is very expensive, because they consist of a great number of individual parts, some of which are of a complicated shape, which cause high manufacturing costs and assembly costs.

In another prior-art tubular-shaft instrument (DE G 93,07,793.9), the actuating rod is made as a one-piece, continuous rod, and it is directly connected to the actuating lever. The guide tube with the tool arranged at its end, which may be, e.g., gripping forceps, scissors or the like, can freely rotate in both directions around the axis of the guide tube in relation to the holder; however, neither the guide tube nor the actuating rod can be removed from the holder. The actuating rods cannot be detached from the actuating lever, either. This makes cleaning and sterilization, which must be performed after each use, very difficult.

SUMMARY AND OBJECTS OF THE INVENTION

The primary object of the present invention is to design a tubular-shaft medical instrument of the class described in the introduction such that it can be manufactured especially more inexpensively and be disassembled more easily for cleaning and can then be assembled to a ready-to-use state in a simple manner.

This object is attained according to the present invention by the actuating rod passing through the guide sleeve in one piece and being detachably connected to the actuating lever by a rod coupling, and that the guide tube is rigidly and especially nonrotatably connected to the guide sleeve.

The principal advantage of such a design can be considered to be the fact that the instrument consists of a substantially smaller number of individual parts, which are also simpler, so that it can be manufactured at a substantially lower cost. Even though only the actuating rod and the surgical instrument operated by it can be detached from the holder and be pulled out of the guide tube, this possibility of partial disassembly is completely sufficient for separate cleaning or sterilization. In addition, handling is simpler and easier in many respects, and the instrument is again completely able to function after assembly, which can be performed with simple movements.

The embodiment of the invention which in the area of the guide sleeve the actuating rod has at least one lateral rotation-preventing surface leads to a highly favorable design in terms of space requirement and function for the securing means necessary for securing the connection between the tube section of the tool and the guide tube, which connection is detachable but fixed in the ready-to-use state. It is further advantageous according to the invention to use two rotation-preventing bolts, which are diametrically opposed and are arranged coaxially to one another. The embodiment of the invention wherein the rotation-preventing bolt or bolts are mounted in a radial hole of the guide sleeve and can be engaged with and disengaged from the rotation-preventing surface makes possible, along with a simple design, a simple and easy manual operation of the securing means for detaching the connection between the tube section of the tool and the guide tube, and it should be emphasized that unintended, spontaneous detachment of the rotation-prevention means is completely ruled out.

While it is possible, in principle, to provide crank-like guide surfaces in the slider sleeve to operate the rotation-preventing bolts, a very simple, operationally reliable possibility of operating the rotation-prevention means is created by the provision of a slider sleeve which has as an oblique surface an inner cone with which the rotation-preventing bolts are in spring mounted contact.

The invention preferably is provided with a slider sleeve which is under the action of an axial spring force by which the rotation-preventing bolt is brought into and maintained in a positive locking engaged position with the rotation-preventing surfaces of the actuating rod. The slider sleeve is provided with a slide grip which surrounds the slider sleeve and is comprised of an electrically non-conductive plastic. The guide sleeve is rigidly connected to the coaxial bearing bush which in turn is mounted rotatably but axially immovably in a bearing hub of the locking flange. The bearing hub is fastened in the holder and a rotation position-locking means is provided between the guide sleeve and the locking flange. The guide sleeve is provided with a turning grip formed of an electrically non-conductive plastic. The rear end of the actuating rod is preferably provided with a coupling head that is thicker than the rear, cylindrical rod section, and the actuating lever has a coupling sleeve, which is displaceable at right angles to the system axis, in the cavity, in which the keyhole like coupling opening is located.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side view of a complete tubular-shaft surgical instrument with a forceps-like tool;

FIG. 2 is a side view of a section of the front end section of the guide tube with the forceps-like tool;

FIG. 3 is an enlarged section III—III from FIG. 2;

FIG. 4 is an enlarged sectional view of the tool head according to FIG. 2 with opened tool;

FIG. 5 is an enlarged sectional view V—V from FIG. 4;

DETAILED DESCRIPTION OF THE PREFERRED EMBODIMENTS

Figure 8:
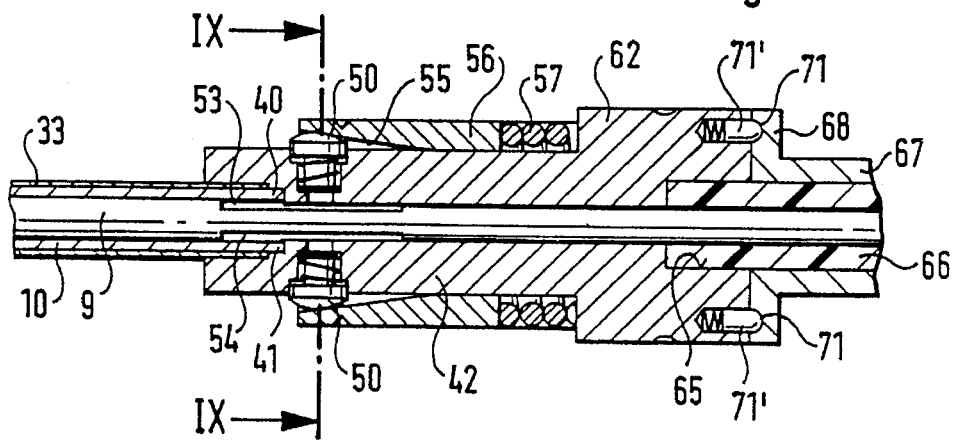
FIG. 8 is a cross sectional view showing parts from FIG. 4 in another functional position, with some of the parts having a different shape.
Figure 9:
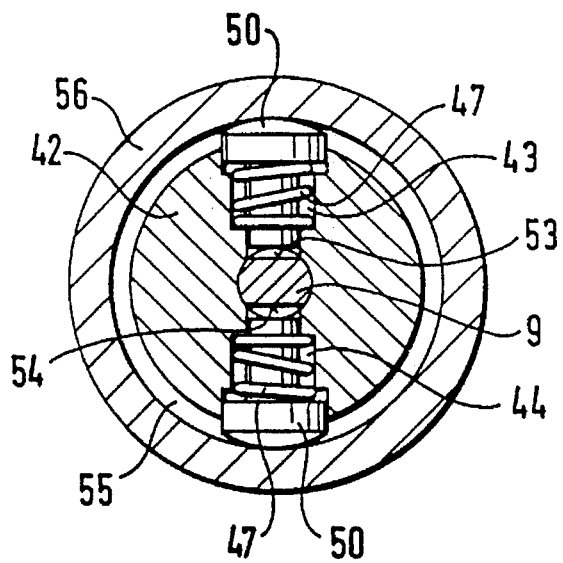
FIG. 9 is a sectional view IX—IX from FIG. 8.
Figure 9A:
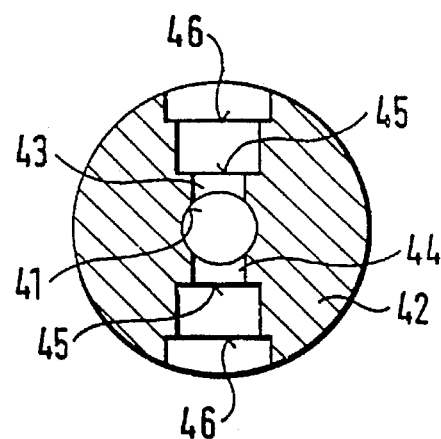
FIG. 9a is a sectional view of the two radial holes of the guide sleeve.

The tubular-shaft surgical instrument 1 shown in the drawing has a gripping forceps 3 as the surgical tool at the front, free end of a guide tube 10 coaxial with a system axis 2. The gripping forceps 3 is comprised of two gripping jaws 6 and 7, which are pivotably mounted on a common hinge pin 5 (FIGS. 2 and 4) around a common pivot axis extending at right angles to the system axis 2, and which are in a hinged connection with a cylindrical actuating rod 9 via a thinner, cylindrical rod section 9' through a scissors hinge 8, and the said actuating rod 9 is mounted axially movably in the guide tube 10 (FIGS. 8 and 9). The gripping jaws 6 and 7 can be opened by axially displacing the actuating rod 10 in the direction of the arrow 11, and they can be closed in the direction of arrow 12. The two gripping jaws 6 and 7 are accommodated by flattened, short lever arms 21 and 22, respectively, in a slotlike opening 13 of a separate tube section 14 cut out in a fork-like pattern, with the hinge pin 5 being fastened in mutually coaxial cross holes in the fork-like cheeks of the separate tube section 14 separated by the opening 13. The scissors hinge 8 has two scissors plates 17 and 18, which are connected to the lever arms 21 and 22 of the two gripping jaws 6 and 7 by hinges 19 and 20, and to the rod section 9' of the actuating rod 9 by a common hinge 23.

The tube section 14 designed as a separate support part has a central axial hole 28, in which the rod section 9', which establishes the connection to the hinge 23 and to the gripping jaws 6 and 7, is mounted axially movably.

On the front side 30 facing the actuating rod 9, the tube section 14 has a centering sleeve 31, which has an external diameter approximately corresponding to the actuating rod 9, and which can be fittingly introduced into the front open end 32 of the guide tube 10 provided with a plastic jacket 33. This centering sleeve 31 is provided at its end with two radial, diametrically opposite projections 34 and 35, which have the shape of narrow fingers provided on both sides with mutually plane-parallel surfaces 36 and 37 and have the function of coupling pins of a bayonet catch. The end 32 of the guide tube 10 facing the tube section 14 is provided with two diametrically opposite, L-shaped coupling slots 38 and 39 (FIG. 6), into which the projections 34 and 35 of the centering sleeve 31 of the tube section 14 can be introduced in the manner of a bayonet catch to establish a stable connection, and from which they can again be removed. As a result, the tube section 14 with the gripping forceps 3 along with the actuating rod 9 can easily be pulled out of and reinserted into the guide tube 10, so that these two assembly groups are available separately for the purpose of cleaning or sterilization, and thus they can be treated in a more simple manner and especially more thoroughly. It is important in this connection for the tube section 14 to be able to be connected axially immovably to the guide tube 10, so that the axial movements of the actuating rod 9 can bring about the opening and closing of the gripping forceps 3.

Figure 6:
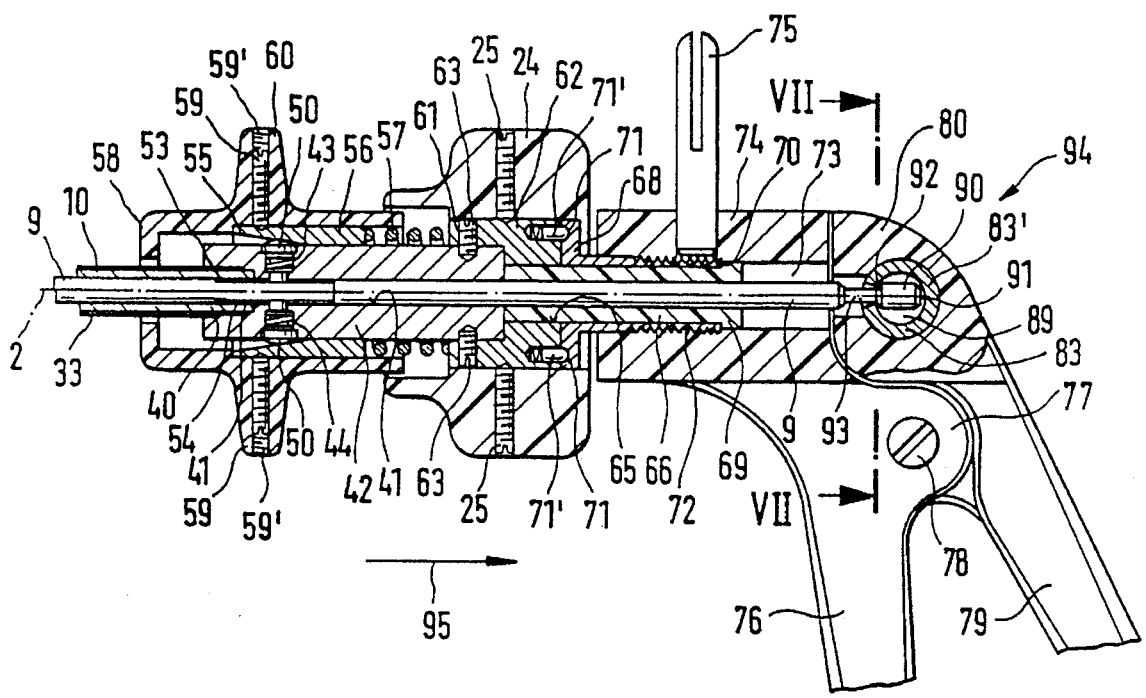
FIG. 6 is a sectional view of the actuating part of the tubular-shaft instrument.
Figure 10:
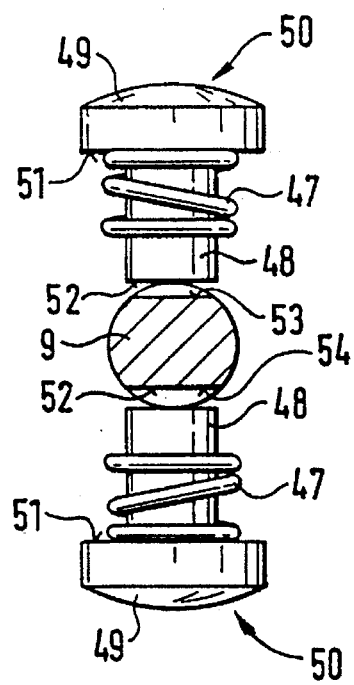
FIG. 10 is an enlarged sectional view of the rotation-preventing section of the actuating rod with two rotation-preventing bolts.

The opposite, rear end 40 of the jacketed guide tube 10 is firmly fastened, e.g., welded, in a coaxial plug hole of a guide sleeve 42. Different embodiments of this guide sleeve 42 are shown in FIGS. 6 and 8. The guide sleeve 42 shown in FIG. 6 has a cylindrical design as a whole, it is provided with a central axial hole 41, and it is dimensioned such that it guidingly accommodates the actuating rod 9 with a small radial clearance. In the vicinity of the plug hole 41, this guide sleeve 42 is provided with mutually coaxial and diametrically opposite radial holes 43 and 44, in which radially movable rotation-preventing bolts 50 are mounted. These radial holes 43 and 44 have two ring shoulders 45 and 46 each, which are formed by diameter expansions. The ring shoulder 45 of smaller diameter is used as a support for a compression spring 47, which surrounds the cylindrical guide shaft 48 of the rotation-preventing bolt 50 provided with a cylindrical round head 49. The second ring shoulder 46 of the larger diameter is used as a radial stop for the round head 49 of the rotation-preventing bolt 50. The radially outer end of the compression spring 47 is in contact with the underside 51 of the round head 49 (cf. FIG. 10).

The two rotation-preventing bolts 50, which are arranged mirror-symmetrically and consequently also coaxially opposite one another in the holes 43 and 44, have flat front surfaces 52 at the radially inner ends of their two guide shafts 48. The rotation-preventing bolts 50 are in contact with these flat front surfaces 52 on one of two diametrically opposite, plane-parallel rotation-preventing surfaces 53 and 54 of the actuating rod 9, respectively. These rotation-preventing surfaces 53, 54 are arranged in the area of the actuating rod 9, which moves during the lifting movements of the actuating rod 9 in relation to the front surfaces 53 of the two rotation-preventing bolts 50. They are formed by two lateral flattened areas.

The two rotation-preventing bolts 50 with their rounded round heads 49 are pressed by the radially outwardly acting compression springs 47 against an oblique surface 55, which extends at an acute angle to the system axis 2 and is designed as the inner cone of a slider sleeve 56. This slider sleeve 56 is under the action of a compression spring 57 surrounding the guide sleeve 42, and it is provided with a slider grip 48, which is made of a nonconductive plastic, completely surrounds it, and is firmly connected to it by radial locking screws 59. These locking screws 59 are screwed into radial holes 59' of two diametrically opposite radial fingers 60 of the slider grip 58. The end of the compression spring 57 facing away from the slider sleeve 46 is in contact with a ring-shaped front surface 61 of a cylindrical ring body 62, which is connected to the rear end of the guide sleeve 42 both nonrotatably and immovably in the axal direction. This ring body 62 is surrounded by a turning knob 24 consisting of plastic, which is rigidly connected to it by radial locking screws 25.

The ring body 62 has a central cylindrical axial hole 65, in which a bearing bush 66 made of plastic is fastened axially immovably, and the connection may be established by a thread, by bonding or by welding. This bearing bush 66 is rotatably mounted in the bearing hub 67 of a locking flange 68 and is provided at its rear end with a ring shoulder 69, which is in contact with the rear front surface 70 of the bearing hub 67. This guarantees that the locking flange 68 with its bearing hub 67 cannot move in the axial direction in relation to the bearing bush 66. The flat front surface of the locking flange 68, which faces the ring body 62 and is in contact therewith, is provided with a plurality of locking depressions 71 arranged in a ring-like pattern, in which axially spring-tensioned locking pins 72 of the ring body 62 can engage in a locking manner to fix certain angular positions of the turning grip 64 and of the actuating rod 9 or tool 3 nonrotatably engaging it via the rotation-preventing bolt 50 as well as the guide sleeve 42 and the ring body 62.

With threads 72 on its outside, the bearing hub 67 is firmly screwed into the internal threaded section of a hole 73 of a holder 74 made of plastic. An upwardly extending electrical contact pin 75 is located in this holder 74. The holder 74 is provided with an eye grip 76 on its underside. This eye grip 76 has, just under the holder 74, a bearing eye 77, in which an actuating lever 79, likewise designed as an eye grip, is pivotably mounted by means of a bearing journal 78.

In the upper, shorter lever arm 80 of this actuating lever 79 is located, in a cross hole 81, a coupling sleeve 83, which is provided with a pushbutton 82 and is displaceable manually against the action of a pull-back spring 84 in the direction of the arrow 85 at right angles to the system axis 2. This cylindrical coupling sleeve 83 is provided with a radial stop pin 96, which is guided in a slot opening 97 of the lever arm 80. This stop pin 96 prevents the coupling sleeve 83 from rotating in the hole 81, on the one hand, and it holds the coupling sleeve 83 in the coupling position shown in FIG. 7 when the pushbutton 82 is not actuated. In addition, the coupling sleeve 83 has, in its wall 83', a keyhole-like coupling opening 86, which is aligned with the system axis 2 and consists of a round hole 87 and a narrower slot opening 88 directly adjoining the former. The diameter of the round hole 87 is slightly larger than the diameter of the coupling head 90 of the actuating rod 9 extending into the cavity 89 of the coupling sleeve 83. The width w of the slot opening 88 is adjusted to the tapered diameter of a shorter intermediate piece 93, which connects the coupling head 90 to the rest of the actuating rod 9 in one piece. To make it possible to move the actuating rod 9 by the actuating lever 79 in both axial directions, i.e., to push it in the direction of the tool 3 and to pull it in the opposite direction, the coupling head 90 of the actuating rod 9 is designed to be such that it bridges over the cylindrical cavity 89 of the coupling sleeve 83 almost completely in the axial direction of the system axis 2. As a result, the coupling head 90 is in contact with the inside of the coupling sleeve 83 with its rear front edge 91, on the one hand, and with its front, slightly oblique ring shoulder 92, on the other hand, with a small axial clearance.

Figure 7:
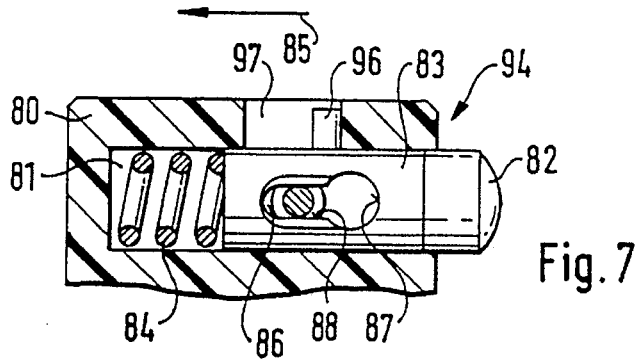
FIG. 7 is a partial section VII—VII from FIG. 6.

In the functional position of the guide sleeve 42, on the one hand, and of the coupling sleeve 83, on the other hand, which is shown in FIGS. 6 and 7, the actuating rod 9 is coupled with the coupling sleeve 83 and, by the latter, with the upper, short lever arm 80 of the actuating lever 79, and it is prevented from rotating in the guide sleeve 42 by the two rotation-preventing bolts 50 that are in contact with the rotation-preventing surfaces 53 and 54, so that the bayonet catch-like connection between the tube section 14 of the tool 3 and the front end of the guide tube 10 is firmly engaged and cannot be detached.

However, if the tool 3 with the actuating rod 9 is to be pulled out of the guide tube 10 for cleaning purposes, it is necessary to displace the slider sleeve 56 on the guide sleeve 42 by means of the slider grip 58 in the direction of the arrow 95, so that the two spring-tensioned rotation-preventing bolts 50 release the two rotation-preventing surfaces 53 and 54 of the actuating rod 9 due to their outward movement, which takes place along the oblique surface 55 that is becoming wider, so that this actuating rod 9 can be rotated to release the bayonet catch-like connection between the tube section 14 and the front end of the guide tube 10. To also release the coupling head 90 at the same time, the coupling sleeve 83 must be moved in the direction of the arrow 85 (FIG. 7) to the extent that the coupling head 90 can leave the coupling sleeve 83 through the round hole 87 of the latter.

It is also necessary to detach the two rotation-preventing bolts 50 by correspondingly displacing the slider sleeve 56 when the actuating rod 9 is reintroduced into the guide sleeve 42.

Because of the upward slope of the oblique surface 55, which has to be small to guarantee automatic interlocking, it is not possible to press the rotation-preventing bolt 50 to the outside when the slider sleeve 56 is not displaced manually to release it.

Introduction of the coupling head 90 into the coupling sleeve 83 also makes it necessary to displace the coupling sleeve 83 in the direction of the arrow 85 to the extent that the coupling head 90 can be led through the larger round hole 87. When the pushbutton 82 is subsequently released, the coupling sleeve 83 is again displaced by the compression spring 84 into the coupling position shown in FIG. 7, in which the thinner section 93 of the actuating rod 9 is located in the narrower slot opening 88, as a consequence of which there is a positive-locking connection between the coupling sleeve 83 and the actuating rod 9.

While the ring body 62 is designed as a separate component in the exemplary embodiment shown in FIG. 6, and it is firmly connected to the guide sleeve 42 by the two radial screws 63 and 64, this ring body 62 is made in one piece with the guide sleeve 42 in the embodiment shown in FIG. 8. As a result, the guide sleeve 42, including the ring body 62, can be manufactured in a simpler manner and at a lower cost.

While specific embodiments of the invention have been shown and described in detail to illustrate the application of the principles of the invention, it will be understood that the invention may be embodied otherwise without departing from such principles.

What is claimed is:

1. A tubular-shaped surgical instrument, comprising: an actuating rod; a guide tube, said actuating rod being guided axially movably in said guide tube; a forceps/scissors-like tool, mounted at a free end of said guide tube, connected to said guide rod, said guide tube having a tube section with a slot cutout, said tool being mounted in said cutout, said tool having at least one tool part pivotable around an axis extending at right angles to an axis of said guide tube, said guide tube having a bayonet catch receiving portion; a bayonet catch associated with said tube section and said tool for detachably mounting said tube section and tool to said guide tube; an actuating lever connected to said actuating rod for actuating said tool; detachable connection means for connecting said actuating rod to said lever; a holder provided with a hand grip, said actuating lever being pivotably mounted on said holder, said holder including a guide sleeve coaxial with said guide tube, said guide sleeve including non-rotation means for preventing said actuating rod from rotating in relation to said guide tube, said detachable connection means including a rod coupling for connecting said actuation rod to said actuating lever, said actuating rod passing through said guide sleeve in one piece, said guide tube being rigidly and non rotatably connected to said guide sleeve.

2. A tubular-shaped surgical instrument according to claim 1, wherein in an area of said guide sleeve, said actuating rod has a lateral, flattened rotation-preventing surface, said non-rotation means including a radially displaceable rotation-preventing bolt, mounted radially displaceable in said guide sleeve, said rotation-preventing bolt being in positive-locking contact with said flat surface.

3. A tubular-shaped surgical instrument according to claim 2, wherein said actuating rod includes an additional flattened rotation-preventing surface, said rotation-preventing means including an additional rotation-preventing bolt, said rotation-preventing bolt and said additional rotation-preventing bolt being provided diametrically opposite and mutually coaxially arranged, for contact with said rotation-preventing surface and said additional rotational-preventing surface respectively.

4. A tubular-shaped surgical instrument according to claim 2, wherein said rotation-preventing bolt is mounted in a radial hole of said guide sleeve; a slider sleeve being provided displaceable on said guide sleeve, said slider sleeve being engageable with and disengageable from said rotation-preventing surface by oblique surfaces of said slider sleeve, said oblique surfaces extending in a self-locking manner and at an acute angle in relation to said system axis.

5. A tubular-shaped surgical instrument according to claim 4, wherein said slider sleeve oblique surface is formed as an inner cone, said rotation-preventing bolts including a head part with rounded off engaging surfaces, a spring element being provided for urging said engaging surfaces into contact with said inner cone.

6. A tubular-shaped surgical instrument according to claim 5, further comprising an axial spring acting on said slider sleeve for maintaining a positive-locking engaged position between said rotation-preventing bolts and said rotation-preventing surface of said actuating rod.

7. A tubular-shaped surgical instrument according to claim 4, wherein said slider sleeve is provided with a slider grip which surrounds said slider sleeve and is formed of electrically non-conductive plastic.

8. A tubular-shaped surgical instrument according to claim 1, further comprising a locking flange with a bearing hub, said coaxial bearing bush being mounted rotatably and axially immovably in said bearing hub, said bearing hub being fastened to said holder; rotation position-locking means disposed between said guide sleeve and said locking flange for preventing relative movement between said guide sleeve and said locking flange.

9. A tubular-shaped surgical instrument according to claim 8, wherein a turning grip is provided formed of electrically non-conductive plastic, said turning grip being formed as part of said guide sleeve.

10. A tubular-shaped surgical instrument according to claim 1, further comprising a coupling head provided at a rear end of said actuating rod, said actuating rod including a rear, cylindrical rod section, said coupling head being thicker than said rear cylindrical rod section, said coupling sleeve being displaceable at right angles to a system axis, said coupling sleeve having a cavity for receiving said coupling head with a keyhole like coupling opening forming a passage into said cavity.

* * * * *